United States Patent
Araki et al.

(10) Patent No.: US 8,768,721 B2
(45) Date of Patent: Jul. 1, 2014

(54) MEDICAL INSTRUMENT MANAGEMENT SUPPORT APPARATUS FOR SUPPORTING SCOPE MANAGEMENT

(75) Inventors: Hiroyuki Araki, Kanagawa (JP); Tatsuya Shiobara, Tokyo (JP); Chieko Watanabe, Tokyo (JP); Nobuaki Matsubara, Saitama (JP); Kazuhiro Akiyama, Tokyo (JP); Hidenori Tsuruma, Tokyo (KP); Tasuku Ogawa, Saitama (JP)

(73) Assignee: Olympus Medical Systems Corp., Tokyo (JP)

( * ) Notice: Subject to any disclaimer, the term of this patent is extended or adjusted under 35 U.S.C. 154(b) by 707 days.

(21) Appl. No.: 12/533,878

(22) Filed: Jul. 31, 2009

(65) Prior Publication Data

US 2010/0030573 A1    Feb. 4, 2010

(30) Foreign Application Priority Data

Jul. 31, 2008 (JP) .................................. 2008-198649

(51) Int. Cl.
  *G06Q 10/00* (2012.01)
  *G06Q 50/00* (2012.01)
  *A61B 5/00* (2006.01)
  *G06F 19/00* (2011.01)

(52) U.S. Cl.
  USPC .................................................. 705/2; 705/3

(58) Field of Classification Search
  USPC ........................................................ 705/2–3
  See application file for complete search history.

(56) References Cited

U.S. PATENT DOCUMENTS

| | | | | |
|---|---|---|---|---|
| 5,289,385 | A * | 2/1994 | Grandone | 702/19 |
| 6,726,620 | B2 * | 4/2004 | Shibata et al. | 600/118 |
| 2008/0317648 | A1 * | 12/2008 | Miyako | 422/300 |
| 2009/0055215 | A1 * | 2/2009 | Giraldo et al. | 705/2 |
| 2009/0089092 | A1 * | 4/2009 | Johnson et al. | 705/2 |
| 2009/0089093 | A1 * | 4/2009 | Johnson et al. | 705/2 |

FOREIGN PATENT DOCUMENTS

| | | |
|---|---|---|
| JP | 2002-15073 | 1/2002 |
| JP | 2002-342476 | 11/2002 |
| JP | 2007-202604 | 8/2007 |
| JP | 2008-117382 | 5/2008 |

OTHER PUBLICATIONS

Japanese Official Action dated May 29, 2012 from related application JP 2008-198649 together with an English language translation.

* cited by examiner

*Primary Examiner* — Joy Chng
(74) *Attorney, Agent, or Firm* — Scully, Scott, Murphy & Presser, P.C.

(57) ABSTRACT

The examination schedule memory unit stores an examination schedule including the starting time and the ending time of each examination. A cleaning capacity memory unit stores cleaning-capacity information that specifies the cleaning capacity of cleaning apparatuses that clean a scope used for the examination. A cleaning schedule generation unit generates a cleaning schedule for cleaning a used scope produced at the end of each examination with cleaning apparatuses having a cleaning capacity required by the cleaning-capacity information stored in the cleaning capacity memory unit. The scope shortage determination unit determines whether or not there will be a shortage of scopes to be used for each examination in accordance with both the examination starting time specified by the above examination schedule and the cleaning ending time specified by the cleaning schedule.

8 Claims, 7 Drawing Sheets

| | 412 | 414 | 416 |
|---|---|---|---|
| FACILITY | ADDRESS | THE NUMBER OF AVAILABLE SCOPES |
| YOUR COMPANY | x x x x x | 10 |
| MEDICAL FACILITY a | a a a a a | 0 |
| MEDICAL FACILITY b | b b b b b | 3 |
| MEDICAL FACILITY c | c c c c c | 2 |

MEDICAL INSTRUMENT MANAGEMENT SUPPORT APPARATUS FOR SUPPORTING SCOPE MANAGEMENT

BACKGROUND OF THE INVENTION

1. Field of the Invention

The present invention relates to a medical instrument management support apparatus for supporting the management of scopes used for an endoscopic examination.

2. Description of the Related Art

Scopes used for endoscopic examinations need to be cleaned every time the examinations are finished. Therefore, an apparatus for cleaning (hereinafter, referred to as a cleaning apparatus), which is used for cleaning used scopes, is installed in a medical facility. Medical facilities stock enough number of scopes and cleaning apparatuses used for the maximum number of examinations at the facilities.

[Patent document No. 1] JP 2007-202604
[Patent document No. 2] JP 2002-15073

In the case where there are multiple cleaning apparatuses, a failure in the operation of even one apparatus will lower the overall cleaning capacity of the cleaning apparatuses. The decreased cleaning capacity may result in the cancellation or the delay of a scheduled examination. In order to avoid the cancellation or the delay of an examination, it is necessary to restock scopes in advance from, for example, an outside maintenance company.

In the past, there were some occasions where the delay in making a request for restocking scopes to a maintenance company, etc., resulted in a delay of the delivery of the scopes, causing the expected arrival time for the restocking to be missed. There were also some occasions as a result where requests for restocking scopes were made even when restocking the scopes was not necessary. These result from misjudging whether or not there will be a shortage of scopes in the course of an examination schedule of a day.

SUMMARY OF THE INVENTION

According to one embodiment of the invention, a medical instrument management support apparatus comprises: an examination schedule memory unit operative to store an examination schedule including the starting time and the ending time of each examination; a cleaning capacity memory unit operative to store cleaning-capacity information that specifies the total cleaning capacity of all cleaning apparatuses that clean a scope used for the examination; a cleaning schedule generation unit operative to generate, in accordance with an examination schedule stored in the examination schedule memory unit, a cleaning schedule for cleaning a used scope produced at the end of each examination, with the cleaning apparatuses having a cleaning capacity required by the cleaning-capacity information stored in the cleaning capacity memory unit; and a scope shortage determination unit operative to determine whether or not there will be a shortage of scopes to be used for each examination in accordance with both the examination starting time specified by the examination schedule and the cleaning ending time specified by the cleaning schedule.

Optional combinations of the aforementioned constituting elements, and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Figure 1:
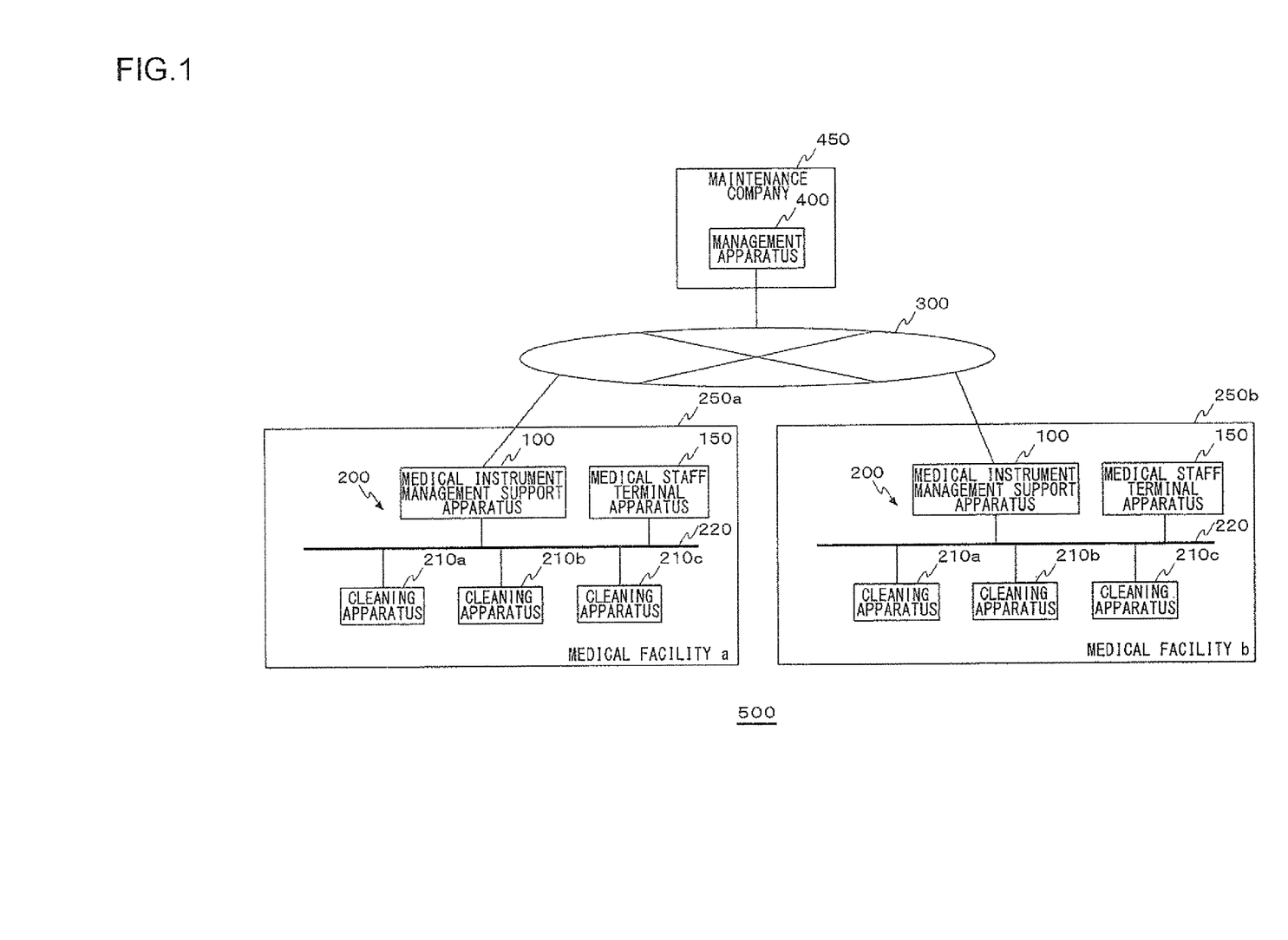
FIG. 1 is a view showing the whole configuration of a medical-instrument restocking system according to the embodiment 1 of the present invention.

FIG. 1 is a view showing the whole configuration of a medical instrument restocking system 500 according to the embodiment 1 of the present invention. The medical instrument restocking system 500 is provided with a management apparatus 400 to be installed at a maintenance company 450 and with medical instrument management support systems 200 each to be installed at each of medical facilities 250a and 250b. The management apparatus 400 and the medical instrument management support systems 200 are connected via an external network 300 such as Internet. The medical instrument management support system 200 has a medical instrument management support apparatus 100, a medical staff terminal apparatus 150, and each of cleaning apparatuses 210a, 210b, and 210c. These apparatuses are connected to one another via an internal network 220 such as intranet. The number of the medical facilities 250a and 250b and the number of the cleaning apparatuses 210a, 210b, and 210c are intended to be illustrative only and are not intended to be limited to the numbers illustrated in FIG. 1.

The maintenance company 450 has concluded the repair and maintenance contract with the medical facilities 250a and 250b for the cleaning apparatuses 210a, 210b, and 210c. In the case of the failure of the cleaning apparatus 210a in the medical facility 250a, a service engineer of the maintenance company 450 repairs the apparatus. The maintenance company 450 provides the service of renting or selling scopes to the medical facilities 250a and 250b. Upon the receipt of a request for restocking scopes (described in detail hereinafter) by the management apparatus 400 in the maintenance company 450 from the medical instrument management support apparatus 100 in the medical facility 250a, the maintenance company 450 delivers the requested number of scopes to the medical facility 250a, which is the client, on the same day.

The medical instrument management support apparatus 100 supports the management of scopes. The medical instrument management support apparatus 100 may be configured as a function of an endoscope management system that manages the overall endoscopic examination. The medical instrument management support apparatus 100 is described in detail hereinafter.

The medical staff terminal apparatus 150 is a terminal that can be referred to by, for example, a doctor, a nurse, or a worker in charge of a cleaning task. A PC placed in, for example, a treatment room, an examination room, or a nurse station and a portable terminal apparatus such as a PDA (Personal Digital Assistant), which a nurse carries, represents the medical staff terminal apparatus 150. This portable terminal apparatus can communicate wirelessly with the medical instrument management support apparatus 100 via an access point on the internal network 220.

The cleaning apparatuses 210a, 210b, and 210c clean and sterilize scopes used for examinations. Unique identification information for self-identification is provided to each scope. For example, an IC tag using the RFID (Radio Frequency IDentification) method is attached to the cord of a scope. The cleaning apparatuses 210a, 210b, and 210c each have a function of retrieving the self-contained identification information of a scope. Upon the completion of cleaning the scope, the cleaning apparatuses 210a, 210b, and 210c each transmit a cleaning-completion notice including the identification information of the scope and the cleaning ending time to the medical instrument management support apparatus 100 via an internal network 220. The cleaning apparatuses 210a, 210b, and 210c may retrieve the identification information for the unique identification of a worker in charge of a cleaning task from an IC tag the worker is wearing and may include the identification information in the cleaning-completion notice. Also, the cleaning-completion notice may be transmitted to the medical staff terminal apparatus 150 of the intended worker.

When a scope cannot be cleaned due to, for example, a failure in the inside of the apparatus or the lack of sterilization solution, the cleaned apparatuses 210a, 210b, and 210c transmit an operation-impossible notice to the medical instrument management support apparatus 100 via the internal network 220. Described above is based on the premise that the cleaning apparatuses 210a, 210b, and 210c have communication functions. However, if the cleaning apparatuses 210a, 210b, and 210c do not have communication functions, the cleaning-completion notice and the operation-impossible notice may be entered manually by a nurse or by a worker in charge of a cleaning task into portable terminal apparatuses that they have and may be transmitted from the portable terminal apparatuses. Also, the notice may be entered to and then transmitted from a PC in the room where the cleaning apparatuses 210a, 210b, and 210c are placed.

Figure 2:
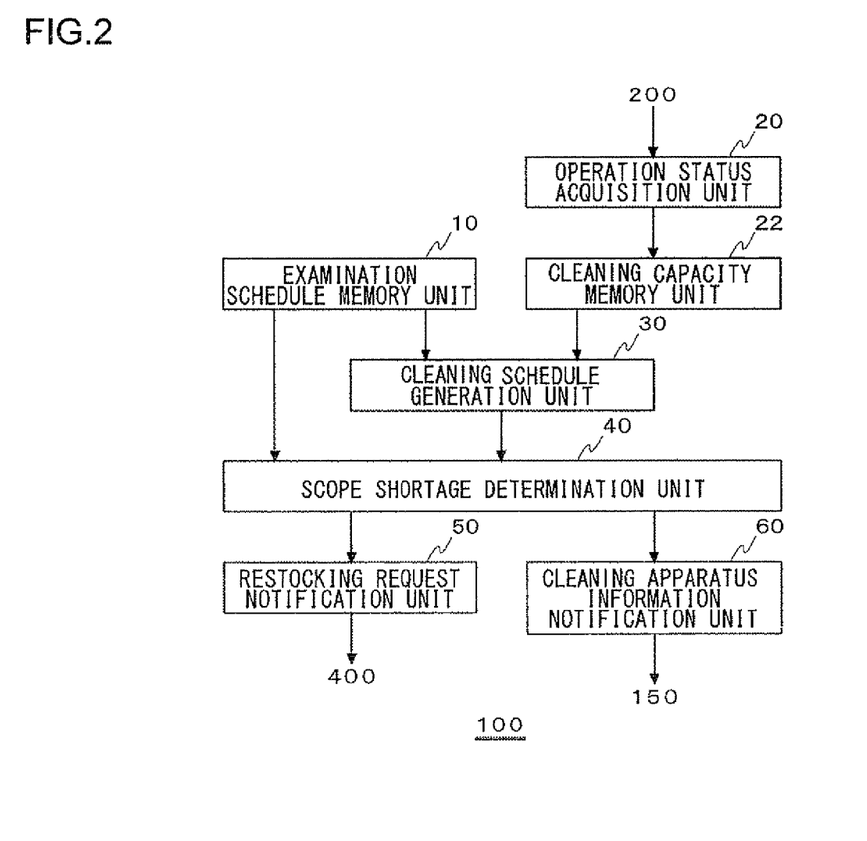
FIG. 2 is a functional block diagram showing the configuration of a medical-instrument-management support apparatus according to the embodiment 1.

FIG. 2 is a functional block diagram showing the configuration of a medical instrument management support apparatus 100 according to the embodiment 1. The medical instrument management support apparatus 100 includes an examination schedule memory unit 10, an operation status acquisition unit 20, a cleaning capacity memory unit 22, a cleaning schedule generation unit 30, a scope shortage determination unit 40, a restocking request notification unit 50, and a cleaning apparatus information notification unit 60.

The configuration of the medical instrument management support apparatus 100 is implemented in hardware by any CPU of a computer, memory or other LSI's, and in software by a program or the like loaded into the memory. Functional blocks are implemented by the cooperation of hardware and software. Thus, a person skilled in the art should appreciate that there are many ways of accomplishing these functional blocks in various forms in accordance with the components of hardware only, software only, or the combination of both.

The examination schedule memory unit 10 stores an examination schedule including the starting time and the ending time of an examination. The examination schedule is generated by a doctor based on an examination order. However, since the subject invention is not focused on a method of generating an examination schedule, the subject is pursued based on the premise that an examination schedule for a day is given and stored in the examination schedule memory unit 10. When multiple examination rooms are established, multiple examinations can be performed concurrently. A specific example of an examination schedule will be described in detail hereinafter.

The examination schedule is limited to those examinations where a scope is used. Furthermore, one examination schedule is generated for each type of scope to be cleaned in the same cleaning apparatus in the embodiment. For example, when a scope for an upper gastrointestinal tract and a scope for a lower gastrointestinal tract are each to be cleaned in an exclusive cleaning apparatus, both an examination schedule for the examinations where a scope for an upper gastrointestinal tract is used and an examination schedule for the examinations where a scope for a lower gastrointestinal tract is used are generated separately.

The cleaning capacity memory unit 22 stores cleaning capacity information that specifies the cleaning capacity of cleaning apparatuses that cleans a scope used for an examination. More specifically, the cleaning capacity memory unit 22 stores as the cleaning capacity information quantity information specifying the number of the operable cleaning apparatuses among multiple cleaning apparatuses. For example, if four cleaning apparatuses are installed and if one is not operable, the cleaning capacity is 75 percent.

The operation status acquisition unit 20 acquires the operation status of multiple cleaning apparatuses. More specifically, when any one of multiple cleaning apparatuses turns not to be operable, the operation status acquisition unit 20, acquiring the operation-impossible notice, updates the quantity information stored in the cleaning capacity memory unit 22. In other words, the number of operable apparatuses specified by the quantity information decreases by one.

In accordance with the examination schedule stored in the examination schedule memory unit 10, the cleaning schedule generation unit 30 generates a cleaning schedule for cleaning a used scope produced at the end of each examination with cleaning apparatuses having a cleaning capacity required by cleaning-capacity information stored in the cleaning capacity memory unit 22, that is, the number of cleaning apparatuses that are operable.

For example, when there are available cleaning apparatuses among operable cleaning apparatuses at the time a given examination ends, the cleaning schedule generation unit 30 sets the ending time of a cleaning of a used scope produced at the end of the examination to the time obtained by adding the cleaning time of the cleaning apparatus to the ending time of the examination. On the other hand, if all the cleaning apparatuses that are operable at the ending time of an examination are in the process of cleaning, the cleaning schedule generation unit 30 sets the cleaning ending time of a used scope produced at the end of the examination to the time obtained by adding the cleaning time of the cleaning apparatus whose cleaning finishes the earliest to the cleaning ending time of the cleaning apparatus.

The scope shortage determination unit 40 determines whether there will be a shortage of scopes to be used for each examination in accordance with both the examination starting time specified by the examination schedule and the cleaning ending time specified by the cleaning schedule. In that case, whether there will be a shortage of scopes can be determined by simulating the transition of the number of usable scopes. The number of usable scopes is a parameter where the number of cleaned scopes stored in a medical facility is set to be the initial value and where the value decreases upon the start of an examination and increases upon the completion of the cleaning of a used scope in accordance with the cleaning schedule.

For example, the scope shortage determination unit 40 decreases the number of usable scopes at the starting time of each examination and increases the ending time of cleaning a used scope, and if the number of usable scopes goes below zero in the examination schedule, the scope shortage determination unit 40 determines that there will be a shortage of scopes. If the number of usable scopes goes below zero, the scope shortage determination unit 40 can, on the assumption that the scopes are supplied to compensate for the shortage, identify the number of scopes missing from a stock by identifying the number of times when the number of usable scopes goes below zero in the examination schedule. More specifically, every time the number of usable scopes becomes −1, the number of scopes missing from a stock is increased by one. When the number of usable scopes goes below −2, the number of scopes missing from a stock is increased by the absolute value thereof.

Being triggered by the acquisition of the operation-impossible notice by the operation status acquisition unit 20, the scope shortage determination unit 40 may determine whether there is a shortage of the scopes. More specifically, a simulation of the transition of the number of usable scopes may be started. Also, the start of the simulation may be triggered by the manipulation of a medical staff or the start of the simulation may be triggered by a set time.

The scope shortage determination unit 40 can specify an examination and its starting time for which a shortage of scopes is expected. Based on a simulation result of the transition of the number of usable scopes, the scope shortage determination unit 40 can determine the number of examinations that can be performed without any scopes needing to be restocked.

If the scope shortage determination unit 40 determines that there is a shortage of scopes, the restocking request notification unit 50 notifies via an external network 300 the management apparatus 400 of the maintenance company 450 of a request for restocking scopes. The request for restocking scopes includes the number of scopes missing from a stock simulated by the scope shortage determination unit 40. Preferably, the request for restocking scopes accounts for the starting time of an examination which is simulated by the scope shortage determination unit 40 where there is a shortage of scopes. In particular, the earliest starting time among all the starting times of an examination where there is a shortage of scopes is preferably included. The maintenance company 450 can work to deliver scopes to be received before the starting time.

The cleaning apparatus information notification unit 60 notifies the medical staff terminal apparatus 150 of information related to the cleaning apparatus, for example, at least either the information indicating that the cleaning apparatus is not operable or the number of examinations that can be performed via the internal network 220. Information indicating that the request for restocking scopes has been notified to the management apparatus 400 of the maintenance company 450 may also be sent to the medical staff terminal apparatus 150.

Figure 3:
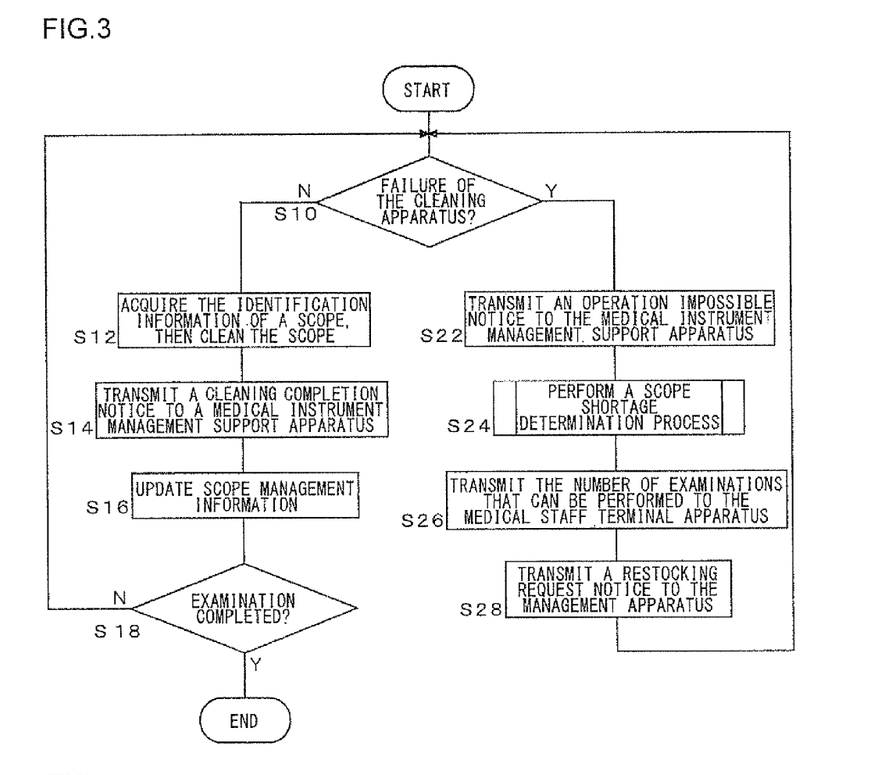
FIG. 3 is a flowchart showing the whole operation of a medical instrument restocking system according to the embodiment 1 of the present invention.

FIG. 3 is a flowchart showing the whole operation of the medical instrument restocking system 500 according to the embodiment 1. The cleaning apparatuses 210*a*, 210*b*, and 210*c* determine whether or not a scope can be cleaned due to, for example, a failure in the inside of the apparatus or the lack of sterilization solution (S10).

If a scope can be cleaned (N in S10), the cleaning apparatuses 210*a*, 210*b*, and 210*c* retrieves the identification information of the scope to be cleaned and then cleans the scope (S12). The cleaning apparatuses 210*a*, 210*b*, and 210*c* transmit the cleaning completion notice to the medical instrument management support apparatus 100 upon the completion of the cleaning of the scope (S14). The operation status acquisition unit 20 of the medical instrument management support apparatus 100 receives the cleaning completion notice from the cleaning apparatuses 210*a*, 210*b*, and 210*c* and updates the scope management information stored in a scope management information memory unit (not shown) (S16). The scope management information memory unit manages multiple scopes stored in the medical facility 250*a* and manages information indicating whether or not each scope is cleaned, in other words, whether or not the scope is usable. Referring to the identification information included in the received cleaning completion notice, the operation status acquisition unit 20 specifies a scope that is already cleaned and changes the scope management information of the scope to "already cleaned."

Upon the completion of all the examinations listed in an examination schedule of the day and the completion of cleaning all the scopes used in the examinations (Y in S18), the overall process is completed. If cleaning all the scopes used in the examinations is not completed (N in S18), the step moves to the step S10 and proceeds with the whole process.

If a scope cannot be cleaned (Y in S10), the cleaning apparatus 210*a* that cannot clean the scope transmits the operation impossible notice to the medical instrument management support apparatus 100 (S22). Upon the receipt of the operation-impossible notice by the operation status acquisition unit 20, the scope shortage determination unit 40 performs a scope shortage determination process (S24). The process will be described in detail hereinafter. The cleaning apparatus information notification unit 60 transmits to the medical staff terminal apparatus 150 the number of examinations that can be performed that is predicted by the scope shortage determination unit 40, based on the premise that the current cleaning capacity of cleaning apparatuses 210*b* and 210*c* in total and that the scopes are not restocked (S26). The cleaning apparatus information notification unit 60 transmits to the management apparatus 400 of the maintenance company 450 both the number and the types of scopes that will be missing from a stock simulated by the scope shortage determination unit 40 (S28). Then, the step moves to the step S10 and proceeds with the whole process.

Figure 4:
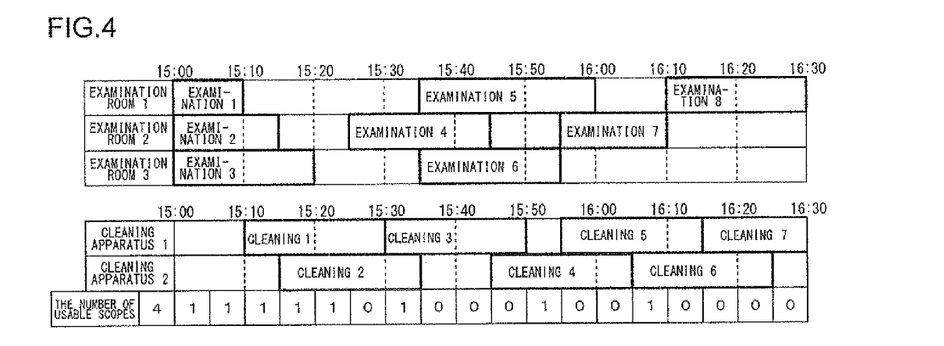
FIG. 4 is a view showing an example of the transition of both an examination schedule and the number of usable scopes (at 100 percent cleaning capacity)

A detailed description will be made hereinafter by using specific examples of the scope shortage determination process. FIG. 4 is a view showing an example of the transition of both an examination schedule and the number of usable scopes (at 100 percent cleaning capacity). A detailed description is now given based on the premise that there are three examination rooms (examination rooms 1-3), two cleaning apparatuses (cleaning apparatuses 1 and 2), and four scopes in the medical facility 250a. This is an example with the operating capacity of the cleaning apparatus at 100 percent. In other words, both the cleaning apparatus 1 and the cleaning apparatus 2 are operable. The cleaning time of the cleaning apparatuses 1 and 2 is 20 minutes for each.

FIG. 4 shows a segment of an examination schedule between 15:00 to 16:30 in the examination schedule for the day. In the figure, it is assumed that the examination schedule for the day is over at 16:30. At 15:00, examinations 1-3 start in the examination rooms 1-3, respectively. As of 15:00, the cleaning apparatuses 1 and 2 are ready and waiting. The number of usable scopes right before 15:00 is four. The examinations 1-3 start at 15:00. Since a scope is used for each examination, the number of usable scopes after 15:00 is one.

The examination 1 in the examination room 1 starts at 15:00 and lasts for 10 minutes, the examination 2 in the examination room 2 starts at 15:00 and lasts for 15 minutes, and the examination 3 in the examination room 3 starts at 15:00 and lasts for 20 minutes. In other words, the examination ending time of the examination 1 is 15:10, the examination ending time of the examination 2 is 15:15, and the examination ending time of the examination 3 is 15:20. Since the cleaning apparatuses 1 and 2 are ready and waiting at the point of 15:10, the cleaning of the scope used for the examination 1 can be started immediately. The cleaning apparatus 1 starts a cleaning 1 at 15:10. Since the cleaning apparatus 2 is ready and waiting at the point of 15:15, the cleaning of the scope used for the examination 2 can be started immediately. The cleaning apparatus 2 starts a cleaning 2 at 15:15.

Since both the cleaning apparatuses 1 and 2 are being cleaned at the point of 15:20, the cleaning of the scope used for the examination 3 cannot be started immediately. Since the ending time of the cleaning 1 in the cleaning apparatus 1 is 15:30 and the ending time of the cleaning 2 in the cleaning apparatus 2 is 15:35, the scope used for the examination 3 is placed in a queue for the cleaning apparatus 1, where the cleaning ends first.

An examination 4 performed in the examination room 2 starts at 15:25 and lasts for 20 minutes. The examination 4 starts at 15:25. Since a scope is used for the examination, the number of usable scopes after 15:25 decreases by one and is therefore zero. The cleaning 1 finishes at 15:30, and the number of usable scopes after 15:30 increases by one and is therefore one. The cleaning apparatus 1 starts a cleaning 3 for the scope used for the examination 3 at 15:30 that is placed in the queue for the cleaning apparatus 1.

The cleaning 2 finishes at 15:35, and then the number of usable scopes increases by one. An examination 5 performed in the examination room 1 starts at 15:25 and lasts for 25 minutes, and an examination 6 performed in the examination room 3 starts at 15:25 and lasts for 20 minutes. Two scopes are used for those examinations. Thus, the number of usable scopes decreases by two. The number of usable scopes increases by one and decreases by two and is therefore zero after 15:35.

The examination 4 finishes at 15:45. Since the cleaning apparatus 2 is ready and waiting at that point, the scope used for the examination 4 can be cleaned immediately. The cleaning apparatus 2 starts a cleaning 4 at 15:45. The cleaning 3 finishes at 15:50, and the number of usable scopes after 15:50 increases by one and is therefore one.

An examination 6 finishes at 15:50. A scope used for the examination 6 does not need to be cleaned immediately since the scope will not be used for any examination for the day. However, the scope is cleaned in preparation for examinations for the next day. The same applies to the scopes used for the examinations 7 and 8. An examination 7 performed in the examination room 2 starts at 15:55 and lasts for 15 minutes. Since a scope is used for the examination, the number of usable scopes after 15:55 decreases by one and therefore becomes zero.

The examination 5 finishes at 16:00. The cleaning 4 finishes at 16:05, and the number of usable scopes after 16:05 increases by one and therefore becomes one. The examination 7 finishes at 16:10. An examination 8 performed in the examination room 1 starts at 16:10 and lasts for 25 minutes. Since a scope is used for the examination, the number of usable scopes after 16:10 decreases by one and therefore becomes zero.

As described, using two cleaning apparatuses and four scopes, all the examinations listed on the examination schedule in FIG. 4 can be performed without any cancellation or delay.

Figure 5:
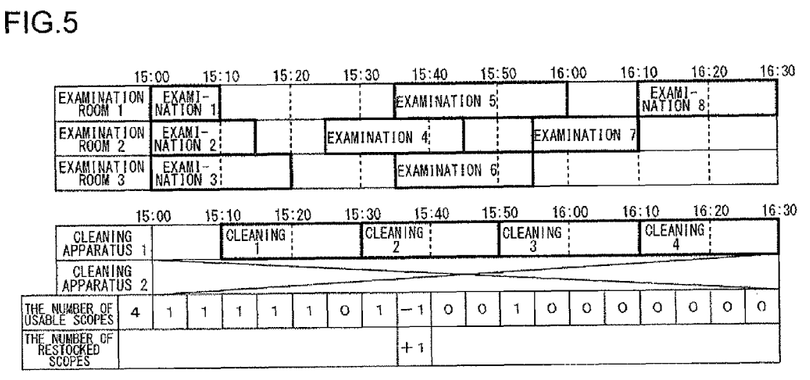
FIG. 5 is a view showing an example of the transition of both an examination schedule and the number of usable scopes (at 50 percent cleaning capacity)

FIG. 5 is a view showing an example of the transition of both an examination schedule and the number of usable scopes (at 50 percent cleaning capacity). The examination schedule is same as the examination schedule in FIG. 4. Note that among two cleaning apparatuses 1 and 2, the cleaning apparatus 2 is not operable, and only the cleaning apparatus 1 is operable. In other words, the operating capacity of the cleaning apparatuses is 50 percent. It is assumed that the cleaning apparatus 2 becomes inoperable at 15:00.

Until 15:10, both the cleanings and the number of usable scopes undergo a transition similar to the one in FIG. 4. An examination 2 finishes at 15:15. Since the cleaning apparatus 1 is in use, the cleaning of the scope used for the examination 2 cannot be started immediately. The scope used for the examination 2 is placed in the queue for the cleaning apparatus 1. An examination 3 finishes at 15:20. The scope used for the examination 3 is also placed in the queue for the cleaning apparatus 1.

The number of usable scopes decreases by one upon the start of an examination 4 at 15:25 and therefore becomes zero, and the number increases by one upon the completion of a cleaning 1 at 15:30 and therefore becomes one. The cleaning apparatus 1 starts a cleaning 2 at 15:30 for the scope used for the examination 2 that has been placed in the queue. At 15:35, examinations 5 and 6 are scheduled to start in the examination rooms 1 and 3, respectively. However, the number of usable scopes at that point is one. In other words, there is a shortage of one scope.

By the medical instrument management support apparatus 100 notifying the management apparatus 400 of the maintenance company 450 of a request for restocking scopes based on this simulation result, the medical facility 250a makes a request to the maintenance company 450 for restocking with one scope by 15:35 For example, if the simulation result comes out at 15:00, the request is sent to the maintenance company 450 at that point. The simulation result after 15:35, explained in the following, is based on the premise that one scope is restocked by 15:35. It is assumed that examinations 5 and 6 both scheduled at 15:35 are performed as scheduled.

An examination 4 finishes at 15:45. The scope used for the examination 4 is also placed in the queue for the cleaning apparatus 1. The number of usable scopes increases by one upon the completion of a cleaning 2 at 15:50 and therefore becomes one. The examination 5 finishes at 15:55. A scope used for the examination 5 does not need to be cleaned immediately since the scope will not be used for any examination for the day. However, the scope is cleaned in preparation for examinations for the next day. The same applies to the scopes used for the examination 6 and other examinations that follow. The number of usable scopes decreases by one upon the start of an examination 7 at 15:55 and therefore becomes zero.

The cleaning apparatus 1 starts a cleaning 3 at 15:50 for the scope used for the examination 3 that has been placed in the queue.

The number of usable scopes increases by one upon the completion of the cleaning 3 at 16:10 and decreases by one upon the start of an examination 8. Therefore, the number of usable scopes after 16:10 is zero.

As described, using one cleaning apparatus and four scopes, all the examinations listed in the examination schedules in FIGS. 4 and 5 cannot be performed. More specifically, either the examination 6 must be cancelled or the start time of the examination 6 must be put off so as to cancel the examinations 7 or 8. In contrast, if one scope is restocked from the outside by 15:35, all the examinations listed in the examination schedules in FIGS. 4 and 5 can be performed without any cancellation or delay.

Figure 6:
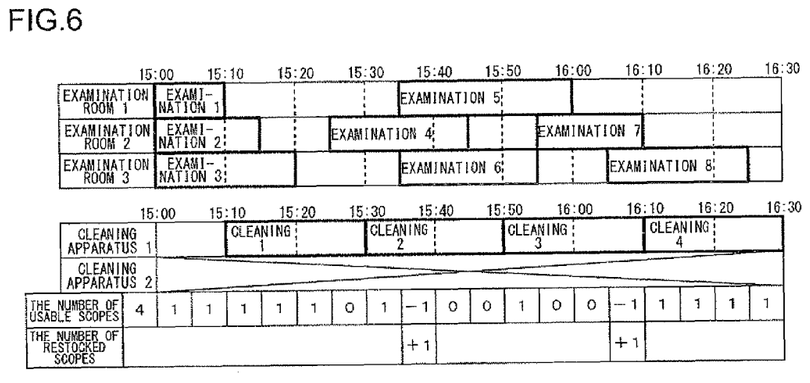
FIG. 6 is a view showing another example of the transition of both an examination schedule and the number of usable scopes (at 50 percent cleaning capacity)

FIG. 6 is a view showing another example of the transition of both an examination schedule and the number of usable scopes (at 50 percent cleaning capacity). The example appears similar to the example in FIG. 5 except that an examination 8 starts five minutes earlier and that more scopes need to be restocked. Differences are described in detail in the following.

The simulation result in FIG. 6 is the same as the simulation result in FIG. 5 up to 16:00. An examination 8 is scheduled in an examination room 1 at 16:05. The number of usable scopes at that point, however, is zero. In other words, there is a shortage of one scope. By notifying with the request for restocking scopes, the medical facility 250*a* requests the maintenance company 450 to restock a total of two scopes: one scope by 15:35; and another scope by 16:05. If the maintenance company 450 has a stock, two scopes can be provided to the medical facility 250*a* by 15:35. In that case, the number of usable scopes from 15:40 to 16:05 may be considered to be increased by one. As in the FIG. 6, it may be also considered that one scope is supplied from the outside at 16:05.

As described, by using one cleaning apparatus and four scopes, all the examinations listed in the examination schedule in FIG. 6 cannot be performed. More specifically, either the examinations 6 and 8 must be cancelled or the start time of the examination 6 must be put off so as to cancel the examinations 7 and 8. In contrast, if one scope is restocked from the outside source by 15:35 and if another scope is restocked from the outside source by 16:05, all the examinations listed in the examination schedule in FIG. 6 can be performed without any cancellation or delay.

Figure 7:
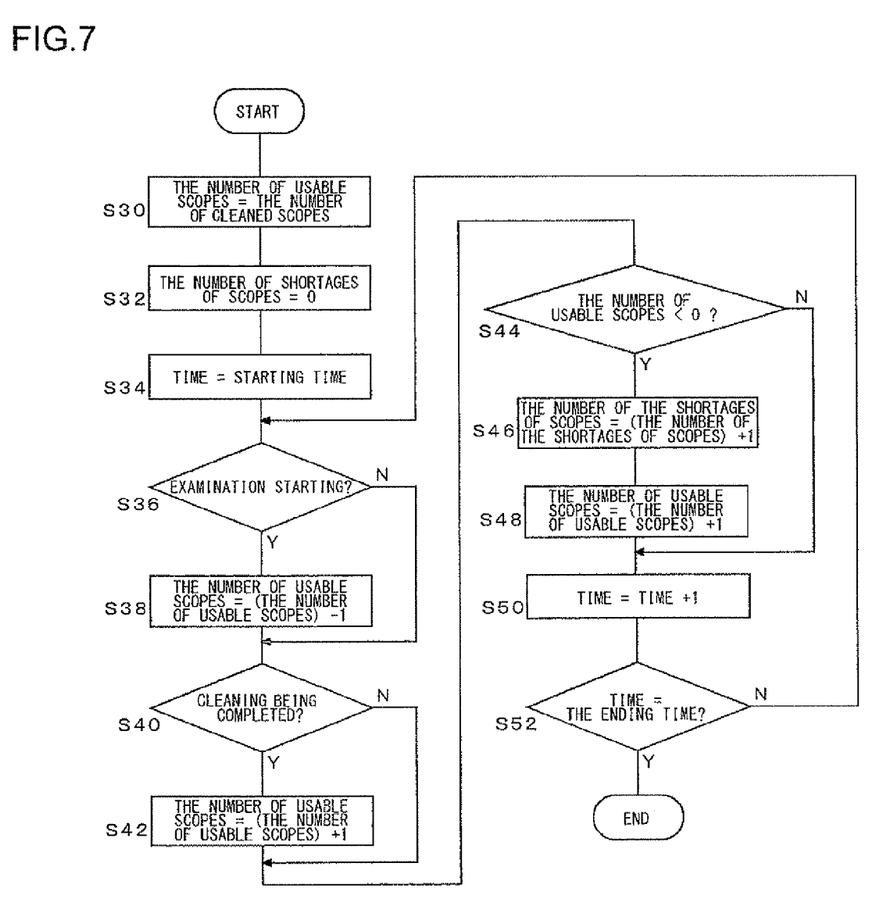
FIG. 7 is a flowchart showing a scope shortage determination process of the medical instrument restocking system according to the embodiment 1.

FIG. 7 is a flowchart showing a scope shortage determination process of a medical instrument restocking system 500 according to the embodiment 1. For the scope shortage determination unit 40 to simulate whether there will be a shortage of scopes, three parameters are used, i.e., "the number of usable scopes," "the number of scopes missing from a stock," and "time." As the setting of the initial values, "the number of usable scopes" is set to the number of cleaned scopes stored in the medical facility 250*a* (S30), "the number of scopes missing from a stock" is set to zero (S32), and the "time" is set to the starting time (S34). The term "starting time" refers to the starting time of the examination schedule for the day or the starting time of the simulation. In the latter case, "the number of usable scopes" is set not to the number of scopes stored in the medical facility 250*a* but to the number of cleaned scopes that are usable at that point. Referring to the above-stated scope management information memory unit, the number of cleaned scopes that are usable at that point can be identified.

Referring to the examination schedule stored in the examination schedule memory unit 10, the scope shortage determination unit 40 determines whether or not there will be any examination that will start at the time indicated by the "time", (S36). If there is any (Y in S36), the value of "the number of usable scopes" is decreased (S38). In FIG. 7, the value is decreased by one. However, if there are multiple examinations that start at the time indicated by the "time," the number of examinations is subtracted from the value of "the number of usable scopes." If there is no examination that starts at the time indicated by the "time" (N in S36), the process of step S38 is skipped.

Referring to the cleaning schedule generated by the cleaning schedule generation unit 30, the scope shortage determination unit 40 determines whether or not there will be any cleanings that will be completed at the "time" (S40). If there is any (Y in S40), the value of "the number of usable scopes" is increased (S42). In FIG. 7, the value is increased by one. However, if there are multiple cleanings that finish at the time indicated by the "time," the number of the cleanings is added to the value of "the number of usable scopes." If there is no cleaning that finishes at the time indicated by the "time" (N in S40), the process of step S42 is skipped.

The scope shortage determination unit 40 determines whether or not the value of "the number of usable scopes" is below zero (S44). If it is below zero (Y in S44), the value of "the number of scopes missing from a stock" is increased (S46). In FIG. 7, the value is increased by one. However, if the value of "the number of usable scopes" is −n (n is an integer of at least 2), n is added to the value of "the number of scopes missing from a stock." Furthermore, the value of "the number of usable scopes" is increased (S48). In FIG. 7, the value is increased by one. However, if n is added to the value of "the number of scopes missing from a stock," n is also added to the value of "the number of usable scopes." If "the number of usable scopes" is at least zero (N in S44), the process of steps S46 and S48 is skipped.

The value of the "time" is increased (S50). More specifically, one minute is added. The scope shortage determination unit 40 determines whether or not the value of the "time" has reached the ending time of the examination schedule (S52). If the value has not reached the ending time (N in S52), the step forwards to the step S36, and the process continues after the step S36. If the value has reached the ending time (Y in S52), the scope shortage determination process is completed. The value of "the number of scopes missing from a stock" at the time of the completion is the number of scopes that will be requested to the maintenance company 450.

A detailed description will be made regarding a method for identifying the number of examinations that can be performed shown in step S26 of the flowchart of FIG. 3, based on the premise that the current cleaning capacity is kept and that the scopes are not restocked. It is found that there is a shortage of scopes in one examination in the simulation result for the examination schedule shown in FIG. 5 and in two examinations in the simulation result for the examination schedule shown in FIG. 6. The simplest method of identifying the number of examinations that can be performed is to subtract the number of examinations where there is a shortage of scopes from the number of all the examinations that follow. The value obtained is specified as the number of examinations that can be performed. The number of the examinations that can be performed is seven for the examination schedule shown in FIG. 5 and six for the examination schedule shown in FIG. 6.

Another method of identifying the number of examinations that can be performed is to collect the past result of examinations for each day along with the cleaning capacity of the day and then to predict by a statistical procedure the number of examinations that can be performed for a given day. In other words, the number of examinations that can be performed with the cleaning capacity of the day is predicted by performing a statistical procedure on collected data. For example, if the number of the examinations that can be performed with the cleaning capacity of the day is predicted to be 18 by using the statistical procedure, and if 20 examinations are scheduled for the day, an examination schedule screen for the day displayed on the display unit of the medical staff terminal apparatus 150 is controlled so as to be changed as follows. For example, for two examinations that are excluded from being counted in the number of the examinations that can be performed, an icon indicating such exclusion is attached and then displayed on the examination schedule screen. A message may be displayed on the examination screen such as: "Due to a failure in the cleaning apparatus, 18 may be the maximum number of examinations that can be performed."

As described above, whether or not there will be a shortage of scopes in the course of an examination schedule of a day can be accurately determined according to the embodiment 1. The number of a shortage of scopes can also be accurately predicted. Therefore, a request for restocking scopes can be made in advance to, for example, an outside maintenance company, and the cancellation or the delay of an examination can be avoided. By determining whether or not there will be a shortage of scopes due to the lowered cleaning capacity of cleaning apparatuses, whether or not there will be a shortage of scopes and, if there will be, the number of scopes that will be missing from a stock can be predicted accurately and promptly. Therefore, there can be a reduction of the number of occasions where a delay occurred in making a request for restocking scopes to a maintenance company, etc., causing the expected arrival time for the restocking to be missed. The number of occasions can be reduced where unnecessary requests for restocking scopes are made or where requests for an excess number of scopes are made.

Also, by notifying the medical staff terminal of the number of examinations that can be performed under the condition where the cleaning capacity of cleaning apparatuses is lowered, a medical staff can determine in advance examinations that need to be cancelled or to be delayed when scopes are not restocked or when the transportation of scopes is delayed. For example, a low-priority examination can be cancelled. Contacting all the patients for multiple examinations scheduled after the cleaning capacity is lowered allows for the determination of examinations that need to be cancelled.

The embodiment 2 is now described in detail. In the embodiment 1, the maintenance company 450 that receives the restocking request notice at the management apparatus 400 delivers scopes stored at the company to a client medical facility. In this regard, in the embodiment 2, scopes can also be delivered from a medical facility of a regional partnership to a client medical facility.

Figure 8:
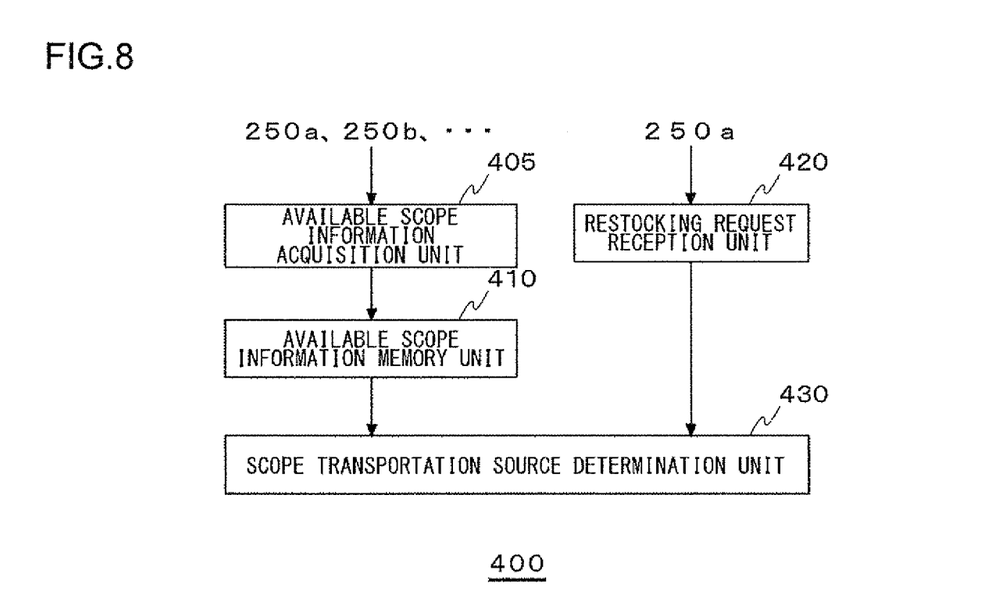
FIG. 8 is a functional block diagram showing the configuration of a management apparatus according to the embodiment 2.

FIG. 8 is a functional block diagram showing the configuration of a management apparatus 400 according to the embodiment 2. The management apparatus 400 includes an available scope information acquisition unit 405, an available scope information memory unit 410, a restocking request reception unit 420, and a scope transportation source determination unit 430.

The available scope information acquisition unit 405 acquires via an external network 300 the available scope information of each medical facility from the medical facilities 250*a*, 250*b*, and onward that have regional partnership with one another. More specifically, the available scope information acquisition unit 405 acquires the number of scopes that are lendable to the outside by each of the medical facilities. The available scope information may be acquired in real time or may be acquired periodically, for example, once a day.

Figure 9:
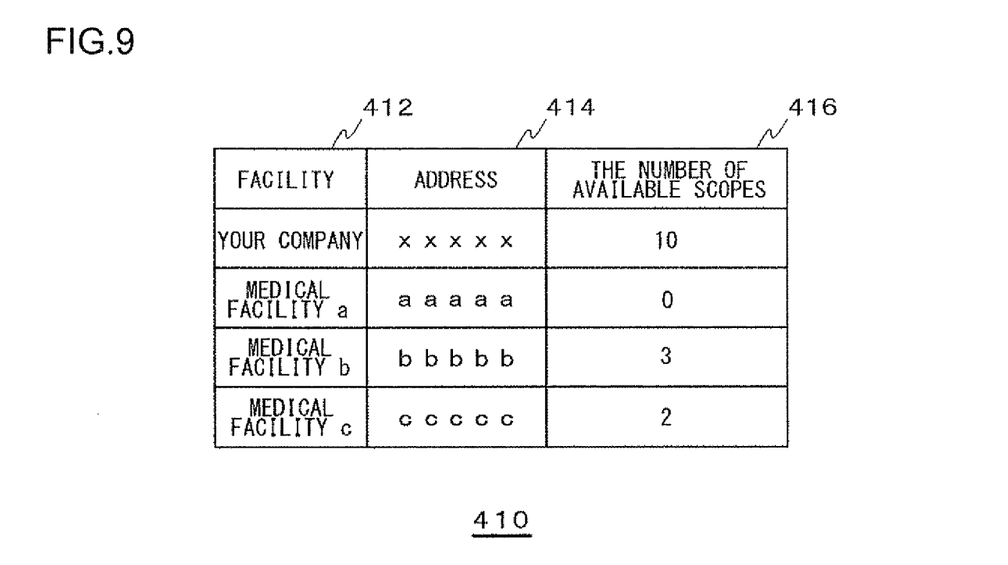
FIG. 9 is a view showing the data structure of an available scope information memory unit according to the embodiment 2.

FIG. 9 is a view showing the data structure of an available scope information memory unit 410 according to the embodiment 2. The available scope information memory unit 410 stores an address 414 and the number of available scopes 416 for every facility 412 that can provide scopes. In FIG. 9, your company (the maintenance company 450) and the medical facilities a, b, and c are registered as the facilities 412 that can provide scopes. The number of available scopes 416 of each of the facilities 412 is updated arbitrarily by an available scope information acquisition unit 405.

Referring back to FIG. 8, the restocking request reception unit 420 receives the restocking request notice via an external network 300 from the medical facility 250*a* where a shortage of scopes is expected upon the receipt of the restocking request notice by the restocking request reception unit 420, the scope transportation source determination unit 430 determines the transportation source by referring to the available scope information memory unit 410. For example, among the medical facilities 412 having available scopes of more than the requested number, the facility 412 geographically closest to the client medical facility 250*a* is determined to be the transportation source. If there is not enough scopes to meet the requested number of scopes at one facility 412, multiple facilities 412 may be determined to transport scopes to the client medical facility 250*a*.

As described above, the following effects along with the effects similar to those of the embodiment 1 can be achieved according to the embodiment 2. In other words, the transportation of scopes from multiple facilities of regional partnerships allows for the shortening of the transportation time from the transportation source to the client medical facility 250*a* so that the scopes can be promptly delivered to the client. Compared to the transportation from only one facility, the transportation of scopes from multiple facilities also allows reducing the number of occasions where the expected arrival time is missed due to a shortage of scopes in the facilities.

The embodiment 3 is now described in detail. In the embodiments 1 and 2, a request for restocking scopes is made to the maintenance company 450 after it is determined that there will be a shortage of scopes. However, the request is not made in the embodiment 3.

Figure 10:
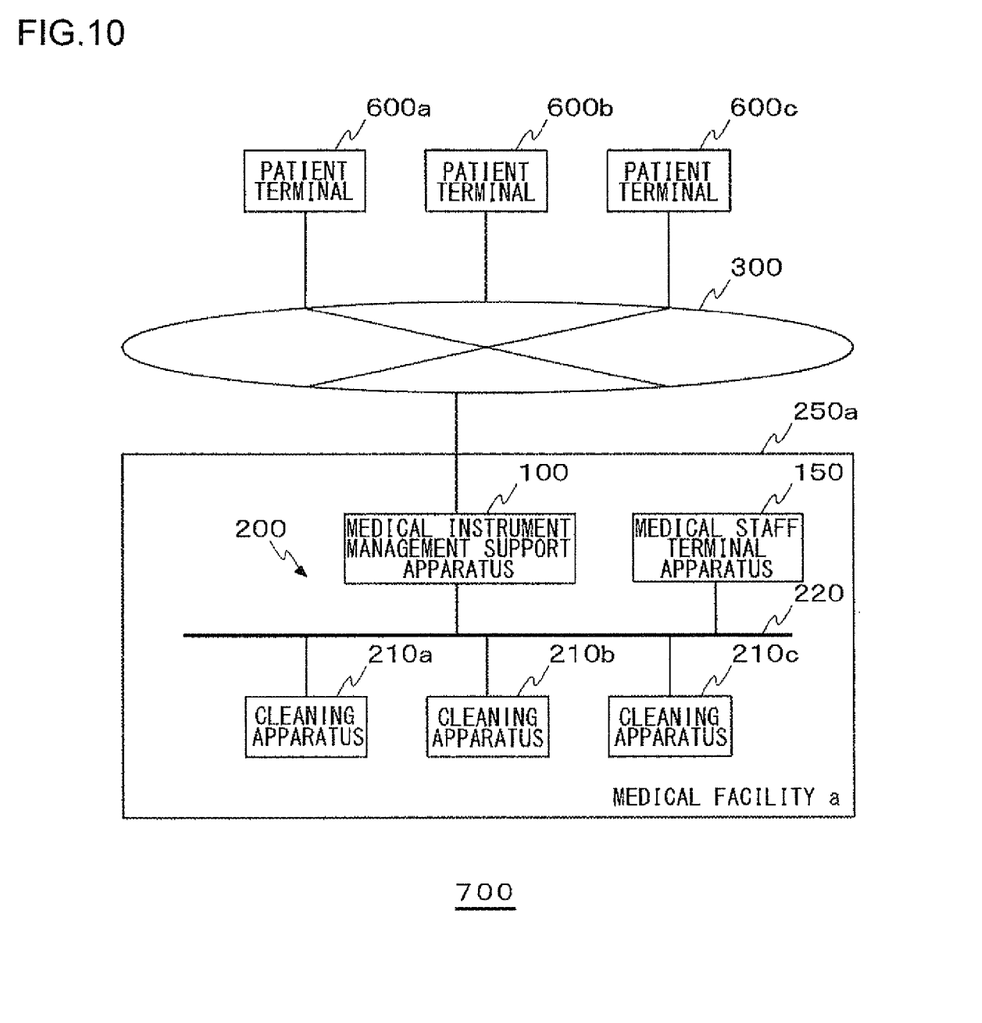
FIG. 10 is a view showing the whole configuration of a medical service support system according to the embodiment 3.

FIG. 10 is a view showing the whole configuration of a medical service support system 700 according to the embodiment 3. The medical service support system 700 is provided with a medical instrument management support system 200 installed in the medical facility 250*a* and with patient terminals 600*a*, 600*b*, and 600*c*. These are connected to one another via an external network 300 such as Internet. The configuration of the medical instrument management support system 200 is similar to the configuration explained in the embodiment 1. Note that the medical instrument management support apparatus 100 does not need to have the restocking request notification unit 50; instead, it includes an examination cancellation information notification unit (not shown).

A PC installed at a patient's house, a cell phone a patient carries, etc., correspond to the patient terminals 600*a*, 600*b*, and 600*c*. The above examination cancellation information notification unit sends via E-mail, etc., to a patient terminal for an examination determined to have a shortage of scopes by the above-stated scope shortage determination process a notification indicating accordingly.

When the number of examinations that can be performed is computed by a statistical method, the value obtained by subtracting the number of examinations that can be performed from the total number of examinations that are scheduled for a day is the number of examinations that may not be able to be performed. The examination cancellation information notification unit transmits via E-mail, etc., notifications, indicating that the examinations may not be offered, to patient terminals of patients scheduled to take examinations that correspond to the examinations whose placements fall within the range of those that may not be able to be performed, as counted from the back of the schedule.

As described above, by identifying the above number of examinations that can be performed and by sending a notification to a patient terminal of a patient scheduled for an examination that will may be or will be cancelled indicating in advance the according information, the patient can become aware of the notification before heading to a medical facility. If a patient receives a cancellation notification, he/she does not need to go to the medical facility on that day. If a patient receives a notification indicating that his/her examination may be cancelled, the patient can check whether or not the examination will be cancelled by phone, etc., in advance before heading to the medical facility. In the former case, a patient can avoid making an unnecessary trip. In the latter case, a patient can most likely avoid making an unnecessary trip.

Described above is an explanation based on the embodiments of the present invention. These embodiments are intended to be illustrative only, and it will be obvious to those skilled in the art that various modifications to constituting elements and processes could be developed and that such modifications are also within the scope of the present invention.

In the above-described embodiment, a shortage is taken into consideration only for the day the cleaning capacity of cleaning apparatuses in total is lowered. However, a simulation may be performed on an examination schedule for a predetermined period from the corresponding day or for a period expected for the cleaning capacity of cleaning apparatuses to return to its original state. With this, a shortage of scopes during a period affected by the lowered cleaning capacity of cleaning apparatuses in total can be easily kept track of.

Instead of being placed in the maintenance company 450 via the external network 300, the management apparatus 400 may be placed in the medical facility 250*a*. This allows for the management of a cleaning apparatus and a scope that are managed at a various locations of the medical facility so that the shortage of scopes can be restored within the medical facility.

In the above-stated simulation of the transition of the number of usable scopes, if a scope is restocked from the outside at a given time, the scope may be cleaned after use and reused for a subsequent examination on the examination schedule of the day. If the cleaning capacity of cleaning apparatuses is high, the number of scopes to be requested for restocking may be reduced by reusing scopes provided for the restocking. The scopes provided for the restocking, of course, do not need to be considered for cleaning and reusing.

In the above-stated embodiment, the example is described where the simulation is triggered by the lowering of the cleaning capacity of cleaning apparatuses in total. The simulation, however, may be performed at the time of planning an examination schedule for a day in order to check whether or not the current number of scopes and the current cleaning capacity of cleaning apparatuses in total will cause a shortage of scopes. If it is determined that there will be a shortage, it is necessary to either modify the examination schedule or restock the scopes.

What is claimed is:

1. A medical instrument management support apparatus, the apparatus comprising:
   an endoscopic examination schedule memory unit operative to store an endoscopic examination schedule including the starting time and the ending time of each endoscopic examination;
   a cleaning capacity memory unit operative to store the number of operable cleaning apparatuses among a plurality of cleaning apparatuses that clean an endoscope used for the endoscopic examination;
   a processor; and
   a memory storing computer readable instructions that, when executed by the processor, implement:
   a cleaning schedule generation unit operative to generate, in accordance with an endoscopic examination schedule stored in the endoscopic examination schedule memory unit, a cleaning schedule for cleaning a used endoscope produced at the end of each endoscopic examination, with as many cleaning apparatuses as the number of operable cleaning apparatuses stored in the cleaning capacity memory unit; and
   an endoscope shortage determination unit operative to determine whether or not there will be a shortage of endoscopes to be used for each endoscopic examination in accordance with both the endoscopic examination starting time specified by the endoscopic examination schedule and the cleaning ending time specified by the cleaning schedule, wherein
   the endoscope shortage determination unit determines whether or not there will be a shortage of endoscopes by simulating the transition of the number of usable endoscopes that decreases upon the start of each endoscopic examination and increases upon the completion of cleaning the used endoscope in accordance with the cleaning schedule, wherein the number of cleaned endoscopes stored in a facility where the endoscopic examination is performed is set to be the initial value,
   the cleaning schedule generation unit sets, when there is an available cleaning apparatus among cleaning apparatuses that are operable at the ending time of the endoscopic examination, the ending time of a cleaning of a used endoscope produced at the end of the endoscopic examination to the time obtained by adding the cleaning time of the cleaning apparatus to the ending time of the endoscopic examination, and sets, when all the cleaning apparatuses that are operable at the ending time of the endoscopic examination are in the process of cleaning, the cleaning ending time of a used endoscope produced at the end of the endoscopic examination to the time obtained by adding the cleaning time of a cleaning apparatus whose cleaning finishes the earliest to the cleaning ending time of the cleaning apparatus, and
   the endoscope shortage determination unit decreases the number of the usable endoscopes at the starting time of each of the endoscopic examinations, increases the ending time of cleaning the used endoscope, and determines that there will be a shortage of endoscopes when the number of the usable endoscopes goes below zero in the endoscopic examination schedule.

2. The medical instrument management support apparatus according to claim 1 wherein the computer readable instructions, when executed by the processor, further implement:
   an operation status acquisition unit operative to acquire the operation status of a plurality of cleaning apparatuses, wherein
   when any one of the plurality of cleaning apparatuses turns out not to be operable, the operation status acquisition unit updates, upon the acquisition of a notice indicating that the cleaning apparatus is not operable, the number of operable cleaning apparatuses stored in the cleaning capacity memory unit.

3. The medical instrument management support apparatus according to claim 2 wherein the endoscope shortage determination unit determines whether there will be a shortage of endoscopes upon the acquisition of the operation-impossible notice by the operation status acquisition unit.

4. The medical instrument management support apparatus according to claim 1 wherein the computer readable instructions, when executed by the processor, further implement:
a restocking request notification unit operative to transmit a request for restocking endoscopes to a management apparatus of a maintenance company via a network, wherein
when the endoscope shortage determination unit determines that there will be a shortage of endoscopes, the restocking request notification unit transmits to the management apparatus a request for restocking the endoscopes.

5. The medical instrument management support apparatus according to claim 1 wherein the computer readable instructions, when executed by the processor, further implement:
a cleaning apparatus information notification unit operative to transmit information related to the cleaning apparatus to a medical staff terminal apparatus, with which medical staff can refer to, wherein
based on a simulation result of the transition of the number of the usable endoscopes, the endoscope shortage determination unit determines the number of endoscopic examinations that can be performed when no endoscope is to be restocked, and
the cleaning apparatus information notification unit reports the number of the endoscopic examinations that can be performed to the medical staff terminal apparatus.

6. The medical instrument management support apparatus according to claim 1 wherein when the number of the usable endoscopes goes below zero, the endoscope shortage determination unit identifies, on the assumption that the endoscopes are restocked to compensate for the shortage, the number of endoscopes that are missing from a stock by identifying the number of times when the number of the usable endoscopes goes below zero in the endoscopic examination schedule.

7. A medical instrument management support method comprising:
storing an endoscopic examination schedule including the starting time and the ending time of each endoscopic examination;
storing the number of operable cleaning apparatuses among a plurality of cleaning apparatuses that clean an endoscope used for the endoscopic examination;
generating using a CPU, in accordance with the endoscopic examination schedule, a cleaning schedule for cleaning a used endoscope produced at the end of each endoscopic examination, with as many cleaning apparatuses as the number of operable cleaning apparatuses; and
determining using the CPU whether or not there will be a shortage of endoscopes to be used for each endoscopic examination in accordance with both the endoscopic examination starting time specified by the endoscopic examination schedule and the cleaning ending time specified by the cleaning schedule, wherein
in the determination of whether or not there will be a shortage of endoscopes, whether or not there will be a shortage of endoscopes is determined by simulating the transition of the number of usable endoscopes that decreases upon the start of each endoscopic examination and increases upon the completion of cleaning the used endoscope in accordance with the cleaning schedule, wherein the number of cleaned endoscopes stored in a facility where the endoscopic examination is performed is set to be the initial value,
in the generation of a cleaning schedule, when there is an available cleaning apparatus among cleaning apparatuses that are operable at the ending time of the endoscopic examination, the ending time of a cleaning of a used endoscope produced at the end of the endoscopic examination is set to the time obtained by adding the cleaning time of the cleaning apparatus to the ending time of the endoscopic examination, and, when all the cleaning apparatuses that are operable at the ending time of the endoscopic examination are in the process of cleaning, the cleaning ending time of a endoscope produced at the end of the endoscopic examination is set to the time obtained by adding the cleaning time of a cleaning apparatus whose cleaning finishes the earliest to the cleaning ending time of the cleaning apparatus, and
in the determination of whether or not there will be a shortage of endoscopes, the number of the usable endoscopes is decreased at the starting time of each of the endoscopic examinations, the ending time of cleaning the used endoscope is increased, and it is determined that there will be a shortage of endoscopes when the number of the usable endoscopes goes below zero in the endoscopic examination schedule.

8. A medical instrument management support apparatus, the apparatus comprising:
an endoscopic examination schedule memory unit operative to store an endoscopic examination schedule including the starting time and the ending time of each endoscopic examination;
a cleaning capacity memory unit operative to store cleaning-capacity information that specifies the total cleaning capacity of all cleaning apparatuses that clean an endoscope used for the endoscopic examination;
a processor; and
a memory storing computer readable instructions that, when executed by the processor, implement:
a cleaning schedule generation unit operative to generate, in accordance with an endoscopic examination schedule stored in the endoscopic examination schedule memory unit, a cleaning schedule for cleaning a used endoscope produced at the end of each endoscopic examination, with the cleaning apparatuses having a cleaning capacity required by cleaning-capacity information stored in the cleaning capacity memory unit; and
an endoscope shortage determination unit operative to determine whether or not there will be a shortage of endoscopes to be used for each endoscopic examination by simulating the transition of the number of usable endoscopes that decreases upon the start of each endoscopic examination and increases upon the completion of cleaning the used endoscope in accordance with the cleaning schedule, wherein the number of cleaned endoscopes stored in a facility where the endoscopic examination is performed is set to be the initial value, wherein
the cleaning schedule generation unit sets, when there is an available cleaning apparatus among cleaning apparatuses that are operable at the ending time of the endoscopic examination, the ending time of a cleaning of a used endoscope produced at the end of the endoscopic examination to the time obtained by adding the cleaning time of the cleaning apparatus to the ending time of the endoscopic examination, and sets, when all the cleaning apparatuses that are operable at the ending time of the endoscopic examination are in the process of cleaning, the cleaning ending time of a used endoscope produced at the end of the endoscopic examination to the time obtained by adding the cleaning time of a cleaning apparatus whose cleaning finishes the earliest to the cleaning ending time of the cleaning apparatus, and the endoscope shortage determination unit decreases the number of the usable endoscopes at the starting time of each of the endoscopic examinations, increases the ending time of cleaning the used endoscope, and determines that there will be a shortage of endoscopes when the number of the usable endoscopes goes below zero in the endoscopic examination schedule.

* * * * *